United States Patent
Poulsen

[11] Patent Number: 5,954,689
[45] Date of Patent: Sep. 21, 1999

[54] JET INJECTOR

[75] Inventor: Jens Ulrik Poulsen, Virum, Denmark

[73] Assignee: Novo Nordisk A/S, Bagsvaerd, Denmark

[21] Appl. No.: 08/987,716

[22] Filed: Dec. 9, 1997

[30] Foreign Application Priority Data

Dec. 20, 1996 [DK] Denmark .................................. 1488/96

[51] Int. Cl.⁶ .................................................... A61M 5/30
[52] U.S. Cl. .............................................. 604/71; 604/211
[58] Field of Search .................................. 604/68, 71, 72, 604/186, 201, 207, 208, 211, 232

[56] References Cited

FOREIGN PATENT DOCUMENTS

WO 95/03844  2/1995  WIPO .
WO 95/27523  10/1995  WIPO .

*Primary Examiner*—Wynn Wood Coggins
*Assistant Examiner*—Sharon Finkel
*Attorney, Agent, or Firm*—Steve T. Zelson, Esq.

[57] ABSTRACT

An injector comprising a changeable cylinder ampoule (2) containing medicine for a number of injections into which ampoule a piston (4) is pressed by a piston rod (9) driven by a drive mechanism to dispense a dose of medicine through a nozzle (5) as a high speed jet which penetrates the skin. The injector comprises a distal part (1) accommodating the cylinder ampoule (2) and a proximal part (8) containing the drive mechanism and the piston rod (9) which can be advanced a set distance by the drive mechanism when released, the distal and the proximal parts being provided with mutually engaging threads so that one of these parts can successively be screwed into the other to set a dose to be delivered by the device.

4 Claims, 1 Drawing Sheet

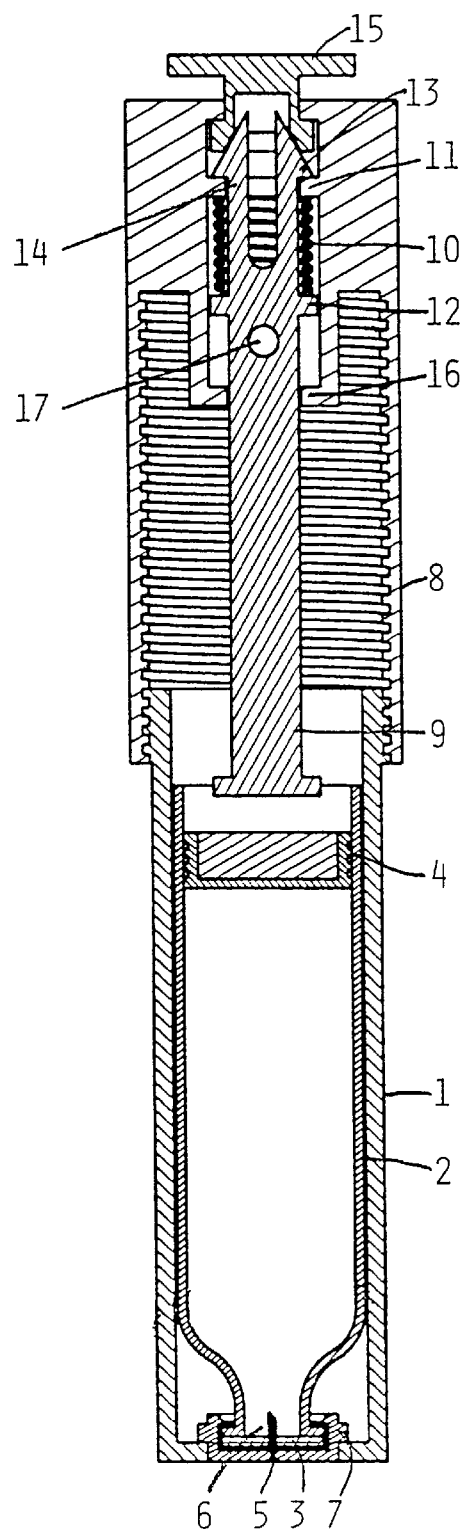
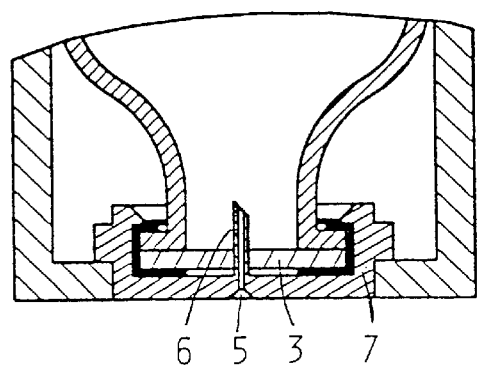
Fig 1
Fig 2

JET INJECTOR

CROSS-REFERENCE TO RELATED APPLICATIONS

The invention relates to jet injectors of the kind comprising a cylinder into which a piston is pressed by a piston rod which when released is driven by a drive mechanism to dispense a dose of medicine through a nozzle as a high speed jet which penetrates the skin.

Unless the injector is delivered as a one shot disposable device which is filled with a medicine dose, an injector has to be filled through its outlet immediately before use, e.g. as described in WO 96/19252. This is an inconvenient process.

BRIEF SUMMARY OF THE INVENTION

Consequently it is an object of the invention to provide a jet injector which is designed to be used for several injections and which do not require a filling procedure in advance of each injection.

This is obtained by a jet injector of the kind described in the opening paragraph of this application which injector is characterised in that the cylinder is a changeable cylinder ampoule containing medicine for a number of injections.

The cylinder ampoule may be of the kind having a first and a second end, wherein a dose of medicine is pressed out through an injection member mounted at the first end when a piston closing the second end is pressed into the ampoule.

Further dose setting means may be provided by which the distance which the piston is moved into the ampoule by the driven piston rod during an injection can be set in advance of each release of the piston rod.

According to the invention the nozzle may be integral with the ampoule or the first end of the ampoule may be closed by a rubber membrane and the injection member may comprise a nozzle mounted in a hub with a needle which penetrates the rubber membrane to make the nozzle communicate with the medicine in the ampoule. The last mentioned embodiment enables a changing of the nozzle between the injections and further the access to the ampoule is closed when the nozzle is dismounted.

In an embodiment of the invention the injector may comprise a distal part accommodating the ampoule and a proximal part containing the drive mechanism and the piston rod which can be advanced a set distance by said drive mechanism when released, the distal and the proximal parts being provided with threads so that one of these parts can successively be screwed into the other to set a dose to be delivered by the device.

BRIEF DESCRIPTION OF THE DRAWINGS

In the following the invention is described in further details with references to the drawing, wherein FIG. 1 schematically shows a sectional view of an injector according to the invention.

FIG. 2 shows in enlarged scale the ampoule end and a mounted injection member.

DETAILED DESCRIPTION OF THE INVENTION

The injector shown in FIG. 1 comprises a distal part 1 accommodating an ampoule 2 which is at an outlet end closed by a rubber membrane 3 and at its other end closed by a piston 4 which can be forced into the ampoule to press out some of the content of the ampoule through a nozzle 5 at the end of a hollow needle 6 which pierces the rubber membrane 3 to make the nozzle communicate with the interior of the ampoule 2 when the nozzle by a hub 7 is mounted on a receiving part at the outlet end of the ampoule. FIG. 2 shows in an enlarged scale the outlet end of the ampoule with the mounted hub 7.

Further the injector comprises a proximal part forming a power unit comprising a housing 8 in which a piston rod 9 is mounted to be moved axially between a proximal and a distal position. In FIG. 1 the piston rod 9 is in its proximal position in which it is held against the force of a spring 10 which positioned between an inward flange 11 in the housing 8 and a ring shaped flange 12 on the piston rod 9 forces the said piston rod in a distal direction. The piston rod is held in its proximal position by a number of hooks 13 provided on flexible arms 14 at the proximal end of the piston rod. Said arms 14 projects through an opening left in the centre of the inward flange 11 so that the hooks grips behind this flange. The hooks present collectively a conical surface on which the edge of an inner bore in a release button 15 can act when the release button is pressed to press hook 13 and the arms inward towards the axis of the piston rod 9 until the hooks loose their grip over the flange 11 and can be drawn through the opening at the centre of said flange 11 when the piston rod 9 by the spring is forced to its distal position which is defined by the ring shaped flange 12 on the piston rod abutting a second inward flange 16 in the housing 8.

From its distal position the piston can be returned to its proximal cocked position by a cocking device comprising a not shown pin which mounted through a hole 17 which runs through the piston rod 9 perpendicularly to the longitudinal axis of this piston rod and which through slots in the housing 8 projects from the outer side of this housing. The ends of this pin can be gripped and manually drawn in a proximal direction to return the piston rod 9 to its proximal position. During this movement of the piston rod 9, the hooks 13 will be moved through the opening at the centre of the inward flange 11 an will due to the flexibility of the arms snap outward and grip behind the flange 11 to lock the piston rod in its proximal position.

The distal part 1 of the injector containing the ampoule 2 is at its proximal end provided with an outer thread which engage an inner thread in the tubular distal end of the housing 8 of the proximal part so that the distal part can be screwed into the proximal part of the injector. This screw connection allows the parts to be screwed apart to allow a changing of the ampoule and to be screwed successively into each other to allow a setting of a dose to be injected.

When a dose is going to be injected, the procedure is the following starting with the piston rod in its distal position:

A hub 7 with a nozzle 5 is mounted on the receiving member at the outlet end of the ampoule 2, the distal part is screwed into the proximal part until a visual inspection shows that medicine is pressed out through the nozzle, the power unit is cocked by drawing the piston in a proximal direction until the hooks 13 grips behind the flange 11 (the end of the piston rod 9 now has a distance to the piston 4 corresponding to the stroke of the piston rod), a dose is set by screwing the distal part into the proximal part a distance corresponding to the movement of the piston which is necessary to press out the wanted dose (the distance between the end of the piston rod 9 and the piston 4 now corresponds to the stroke of the piston rod minus the distance which the piston must be moved to inject the wanted dose), and the nozzle is held against the skin where the injection is wanted and the release button 15 is pressed (the piston rod is now moved by the spring in the distal direction a distance corresponding to its stroke. During the last part of this movement the piston is moved into the ampoule a distance corresponding to the set dose).

A counter may be installed to count units in accordance with the extend of the screwing to set a dose. Further a detent may be provided so that the distal part can only be unscrewed from the proximal part when the detent is released either to allow a partly unscrewing to annul a wrongly set dose or a totally unscrewing to allow changing of the ampoule.

The cocking of the injector may be performed by an build in motor which is powered either from a build in battery or through an external connection to a power source. Also gas pressure from a built in or an external gas cartridge may be used.

In the embodiment described the piston rod is driven by a cocked spring but the piston rod may also be driven by compressed gas, or by an electric motor, or by a carefully adapted charge of an explosive.

I claim:

1. An injector comprising a proximal part and a distal part which parts are provided with co-operating threads so that one part can be screwed into the other part, wherein the distal part accommodates a changeable cylinder ampoule containing medicine, stored between a piston and a closure membrane, for a plurality of injections and a nozzle which communicates, through the closure membrane, with the stored medicine such that medicine is expelled through the nozzle when the piston is pressed into the ampoule, and wherein the proximal part comprises a piston rod and a spring so arranged that the spring can be cocked and released to move the piston rod in a distal direction towards the piston of the ampoule to move the piston into the ampoule to dispense a dose of medicine through the nozzle as a high speed, skin penetrating jet, and a dose setting mechanism by which the distance which the piston rod moves the piston into the cylinder ampoule, when the spring is released, can be set in advance of each release of the spring by screwing one of the distal and the proximal parts a corresponding distance into the other part.

2. An injector according to claim 1, wherein the piston rod is axially moveable, relative to the proximal part, a fixed distance between a release position and a cocked position, wherein the spring is cocked in conjunction with moving the piston rod from the release position to the cocked position, wherein the proximal part and piston rod include cooperating catch members for temporarily holding the piston rod, upon reaching the cocked position, against movement in the distal direction, wherein the proximal part and piston rod include mutually engageable members for stopping the distal movement of the piston rod when the piston rod reaches the release position, and wherein the proximal part includes a release button for releasing the catch members to allow the piston to move in a distal direction towards the release position, whereby the piston rod, when moved from the release position to the cocked position, moves away from the ampoule piston by the said fixed distance, whereby one of the parts may thereafter be screwed into the other part to move the ampoule piston towards the piston rod by a desired distance and thereby set the size of the dose to be administered, and whereby the release button may thereafter be actuated to allow the piston rod to move in a distal direction to the release position and, in so doing, expel the set dose through the nozzle.

3. A method of administering a dose of medicine using an injector having a proximal part and a distal part, which parts include cooperating threads so that one part can be screwed into the other part, wherein the distal part can accommodate an ampoule and the proximal part contains a piston rod having proximal and distal ends, and wherein the piston rod is axially moveable relative to the proximal part; said method comprising the steps of:

(a) inserting an ampoule, containing medicine between a piston and a closure membrane, into the distal part;

(b) moving the piston rod to a release position;

(c) screwing the proximal and distal parts towards one another such that, with the piston rod in the release position, the proximal end of the piston rod abuts the ampoule piston;

(d) providing a nozzle which communicates with the medicine through the closure membrane for expelling a dose;

(e) moving the piston rod in a proximal direction from the release position to a cocked position such that the distal end of the piston rod moves a fixed distance away from the ampoule piston, and such that a spring is cocked to urge the piston rod to move in the distal direction; and, after performing steps (a) through (e), (f) screwing one part into the other part so as to move the ampoule piston a desired distance towards the piston rod to set a desired dose; and, thereafter, (g) releasing the piston rod such that the spring moves the piston rod in a distal direction by the said fixed distance to expel the set dose as a high speed, skin penetrating jet.

4. A method according to claim 3, comprising the steps of temporarily latching the piston rod, upon reaching the cocked position, relative to the proximal part, to hold the piston rod against movement in the distal direction while setting the dose, and thereafter releasing the piston rod when the dose administration is desired.

* * * * *